United States Patent [19]
Iwasaki et al.

[11] Patent Number: 4,770,694

[45] Date of Patent: Sep. 13, 1988

[54] AQUEOUS BIOCIDE SUSPENSION

[75] Inventors: Tesuji Iwasaki; Tsuneyuki Takeno; Yukio Yamamoto, all of Wakayama, Japan

[73] Assignee: Kao Soap Co., Ltd., Tokyo, Japan

[21] Appl. No.: 356,680

[22] Filed: Mar. 10, 1982

[30] Foreign Application Priority Data

Mar. 27, 1981 [JP] Japan ................................ 56-44829

[51] Int. Cl.$^4$ ............................................. A01D 25/22
[52] U.S. Cl. ........................................ 71/93; 71/118; 71/DIG. 1; 424/162; 424/407; 514/143; 514/483

[58] Field of Search ...................... 71/DIG. 1, 93, 118; 424/162; 514/143, 483

[56] References Cited

U.S. PATENT DOCUMENTS 4,313,847   2/1982   Chasin et al. ...................... 71/121 X Primary Examiner—Catherine L. Mills
Attorney, Agent, or Firm—Flynn, Thiel, Boutell & Tanis

[57] ABSTRACT

A water-insoluble biocide component can be effectively dispersed in water by using as a dispersant a phosphoric acid ester salt of a nonionic surfactant.

19 Claims, No Drawings

AQUEOUS BIOCIDE SUSPENSION

This invention relates to a dispersant for an aqueous biocide suspension. More particularly, the present invention relates to a dispersant which is used for preparing an aqueous biocide suspension (flowable formulation) with water being the continuous phase by use of a biocide which is either solid or paste-like at room temperature.

Almost all biocides such as insecticides, fungicides, herbicides, acaricides and the like are substantially water-insoluble. In applying the biocides, therefore, wettable powder has been used, for example, in order to use them as an aqueous suspension but such a suspension involves drawbacks in that caking is likely to occur during storage of the suspension or when the suspension is exposed to high temperature, and the aerial application of ultra-low volume or low volume (4, 8 and 30 times) amounts is not possible.

If the biocide is rendered flowable, on the other hand, it turns into a preparation suitable for aerial application and is free from the problem of caking, but it has been difficult in the past to obtain an aqueous suspension which remains stable for an extended period of time. A variety of surfactants have been employed conventionally in order to obtain a stable aqueous suspension. Examples of the surfactants for this purpose include anionic surfactants such as dialkyl sulfosuccinate salts, alkylbenzenesulfonate salts, naphthalenesulfonate salts or their formalin condensates, ligninsulfonate salts and the like, and non-ionic surfactants such as polyoxyethylene alkyl ethers, polyoxyethylene alkylaryl ethers, polyoxyethylene styrenated phenol ethers, polyoxyethylene tribenzylphenol ethers and the like. These surfactants have been used either alone or in combination. In combination with these surfactants are jointly used water-soluble polymers such as polysaccharides either alone or in combination, as a stabilizer.

However, even when these dispersants and stabilizers are used, the stability of the aqueous suspension has not entirely been satisfactory. In other words, it has been difficult to obtain a suitable viscosity as for the aqueous suspension, or its shelf life (suspension stability) at room temperature or high temperature (40°–50° C.) has not been good. Flocs are likely to occur when the suspension is diluted with water (especially with hard water) and this becomes all the more remarkable when other emulsifiable concentrates are jointly used.

The inventors of the present invention have carried out intensive studies in order to obtain an aqueous biocide suspension which solves all these problems and have found that when a surfactant having a specific chemical structure is used as the dispersant, there can be obtained an aqueous biocide suspension composition which has long shelf life and suspension stability upon dilution and exhibits an excellent effect of preventing flocs from occurring when used in combination with other emulsifiable concentrates, irrespective of the kind of biocides. The present invention has been perfected on the basis of these findings.

Thus, the present invention provides a dispersant for an aqueous biocide suspension which contains a phosphate ester salt of a non-ionic surfactant as the essential ingredient.

The non-ionic surfactant in accordance with the present invention is a non-ionic surfactant having at least one hydroxyl group, and examples of such a surfactant include polyoxyethylene (hereinafter referred to as "POE") alkyl ($C_6$–$C_{22}$) ethers, POE alkyl ($C_4$–$C_{18}$) phenol ethers, polyoxypropylene-polyoxyethylene (block or random) alkyl ethers, POE phenylphenol ethers, POE styrenated phenol ethers, POE tribenzylphenol ethers, and the like.

Among these surfactants, ones which have a benzene ring in the lipophilic group, such as POE alkyl phenol ethers, POE phenylphenol ethers, POE styrenated phenol ethers, POE tribenzylphenol ethers, and the like are preferred. Among them, especially preferred are those non-ionic surfactants which are expressed by the following general formula (I):

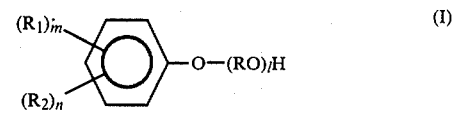

[where $R_1$ is

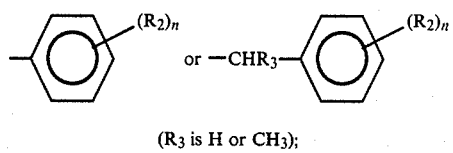

($R_3$ is H or $CH_3$);

$R_2$ is a $C_1$–$C_4$ alkyl group; R is a $C_2$–$C_4$ alkylene group; m is an integer of 1 to 3; n is an integer of 0 to 2; and l is an integer of 1 to 40].

The phosphate ester salt of the non-ionic surfactant in accordance with the present invention can be prepared in the following manner, for example.

0.1 to 1 mol, preferably 0.2 to 0.4 mol, of phosphorus pentaoxide is added to 1 mol of non-ionic surfactant with stirring and is allowed to react with the latter with cooling or heating, whenever necessary, and the reaction product is neutralized.

The compound used for the neutralization is an alkali such as sodium hydroxide, potassium hydroxide, magnesium hydroxide, calcium hydroxide, diethanolamine, triethanolamine, ammonia or the like. Preferred are potassium hydroxide and diethanolamine.

Accordingly, the phosphate ester salt of the present invention has a structure expressed by the following general formula (II):

[where R' is a residue formed when the hydroxyl group is removed from the non-ionic surfactant; M is a counter-ion such as an alkali metal, an alkaline earth metal, ammonium, alkanolamine or the like; and X is R'—O— or —OM].

The mechanism why and how the phosphate ester salt of the present invention exhibits the excellent dispersing and suspending action has not yet been clarified, but the action may be attributable to the peculiar structure expressed by the general formula (II) with the details yet to be clarified. This action is an extremely amazing phenomenon (effect) especially in view of the fact that an acidic phosphate ester which has an analogous structure to that of the phosphate ester salt of the present invention but is not neutralized has a poor dispersing action.

By using the dispersant for an aqueous biocide suspension in accordance with the present invention, it becomes now possible to stably disperse and suspend any water-insoluble biocides which are solid or paste-like at room temperature or the combination of at least two such biocides irrespective of their kinds, and to obtain an excellent flowable biocide composition (flowable preparation).

Examples of biocides that are water-insoluble and solid or paste-like at room temperature are as follows:

Fungicides

Copper agents, mercury agents, organic tin agents, organic arsenic agents, sulfur, organic sulfur agents such as Dithane (zinc ethylenebis(dithiocarbamate)) and Thiuram (bis(dimethylthiocarbamyl)disulfite), organic chlorine agents such as Daconil (tetrachloroisophthalonitrile) and Rabside (4,5,6,7-tetrachlorophthalide) and other compounds such as Captan (N-(trichloromethylthio)-4-cyclohexene-1,2-dicarboxyimide), Difoltan (N-(1,1,2,2-tetrachloroethylthio)-4-cyclohexene-1,2-dicarboxyimide), Acrysid (2-sec-butyl-4,6-dinitrophenyl 3-methylcrotonate), Topsin M (dimethyl 4,4'-o-phenylene-3,3'-dithiodiallophanate), Benrate (methyl 1-(butylcarbamoyl)-2-benzimidazolcarbmate), Takegaren (3-hydroxy-5-methylisoxazole), and so forth.

Insecticides

Organic chlorine type insecticides such as DDT (1,1,1-trichloro-2,2-bis(p-chlorophenyl)ethane), organic phosphorus insecticides having an aromatic ring such as Kayaace (p-dimethylsulfamylphenyl diethyl phosphorothionate), Guardside (2-chloro-1-(2,4,5-trichlorophenyl)vinyl dimethyl phosphate), carbamate type insecticides such as Denapon (1-naphthyl methylcarbamate), Tsumaside (m-tolyl methylcarbamate), Macbal (3,5-xylyl methylcarbamate), Mipsine (o-cumenyl methylcarbamate), Sunside (o-isopropoxyphenyl methylcarbamate), other compounds such as metaldehyde (tetramer of acetaldehyde), Raninate (S-methyl-N-(methylcarbamyloxy)-thioacetimide) and so forth.

Herbicides

Diphenyl ether type herbicides such as Nipp (2,4-dichlorophenyl-p-nitrophenyl ether), MO (p-nitrophenyl 2,4,6-trichlorophenyl ether) and the like, acid amide type herbicides such as Stam (3',4'-dichloropropionanilide), Dimid (N,N-dimethyl-2,2-diphenylacetamide) and the like, carbamate type herbicides such as Swep (methyl 3,4-dichlorocarbanylate) and the like, urea type herbicides such as Carmex D (3-(3,4-dichlorophenyl)-1,1-diethylurea) and the like, triazine type herbicides such as Simazine (2-chloro-4,6-bis(ethylamino)-1,3,5-triazine), Gezaprime (2-chloro-4-ethylamino-6-isopropylamino-1,3,5-triazine), and the like.

Acaricides

Sappirn (p-chlorophenyl p-chlorobenzenesulfonate), Tedion (p-chlorophenyl 2,4,5-trichlorophenyl sulfone), Kelthane (2,2,2-trichloro-1,1-bis(p-chlorophenyl)ethanol), Omite (2(p-tert-butylphenoxy)cyclohexyl propynyl sulfite), and the like.

The phosphate ester salt of the non-ionic surfactant in accordance with the present invention is added to the aqueous biocide suspension composition in an amount of 0.2 to 20 wt% and preferably, 1 to 10 wt%.

Besides water, the biocides and the dispersant, the aqueous biocide suspension composition may further contain a water-soluble tackifier and an anti-foaming agent, whenever necessary. Natural, semi-synthetic and synthetic water-soluble tackifiers can be used as the tackifier. Examples of the natural tackifiers include xanthan gum, xanthane flow, pectin from vegetables, gum arabic and guar gum. Examples of the semi-synthetic tackifiers include methylated products of cellulose or starch derivatives, their carboxyalkylated products and hydroxyalkylated products (including methyl cellulose, carboxymethyl cellulose, hydroxymethyl cellulose and the like) and examples of the synthetic tackifiers include polyacrylates, polymaleates, polyvinylpyrrolidone, and the like.

The water-soluble tackifier is added to the composition in an amount of about 0.01 to about 5 wt% and preferably, about 0.05 to about 1 wt%. There is no limitation as to the anti-foaming agent in particular and polypropylene glycol and silicone oil can be mentioned as particular examples. The amount of the anti-foaming agent is generally up to 2 wt%.

The following is an example of the aqueous biocide suspension composition having good shelf life and excellent flowability which is obtained using the dispersant for the aqueous biocide suspension in accordance with the present invention.

| (A) | biocide | 10–60 wt % |
|---|---|---|
| (B) | phosphate ester salt of non-ionic surfactant | 0.2–20 wt % |
| (C) | water-soluble tackifier | 0.01–5 wt % |
| (D) | anti-foaming agent | 0–2 wt % |
| (E) | water | 20–80 wt % |

In using the dispersant of the present invention, it is possible to jointly use anionic surfactants such as alkyl sulfate salts, alkyl ether sulfate salts, alkyl phenyl ether sulfate salts, alkylnaphthalenesulfonate salts and the like and non-ionic surfactants such as polyoxyethylene alkyl ether, polyoxyethylene alkylphenyl ether and the like so long as the effect of the dispersant is not impeded. Furthermore, it is possible to jointly use a decomposition inhibitor, a flocculation inhibitor (e.g. polyoxyethylene-polyoxypropylene block polymer), a drift inhibitor (e.g. sorbitol), and so forth.

In preparing the aqueous suspension using the dispersant for the aqeuous biocide suspension in accordance with the present invention, the sequence of addition of each component is not limitative in particular.

Next, the present invention will be described with reference to Examples thereof, Comparative Examples and a Testing Example but the present invention is in no way limited thereto.

In the examples which follows, the term "part or parts" represents "part or parts by weight" and the viscosity represents a value measured at 20° C. by a Brookfield viscometer.

EXAMPLE 1

| Tsumaside (m-tolyl methylcarbamate) | 42 parts |
|---|---|
| polyoxyethylene(5.7 mol) styrenated phenol-ether phosphate diethanolamine salt | 5 parts |
| xanthan gum | 0.2 parts |

-continued

| | |
|---|---|
| ethylene glycol | 2 parts |
| anti-foaming agent | 0.2 parts |
| water | 50.6 parts |

The components were weighed and charged into a wet-milling container and were wet-milled (10,000 rpm) for one hour by charging the same weight of glass beads of a 1 mm diameter into the container.

The flowable biocide thus obtained was a suspension having a viscosity of 320 cp and a continuous homogeneous phase and not exhibiting flocculation at all.

COMPARATIVE EXAMPLE 1

| | |
|---|---|
| Tsumaside (m-tolyl methylcarbamate) | 42 parts |
| polyoxyethylene (5.7 mol) styrenated phenol ether | 5 parts |
| xanthan gum | 0.2 parts |
| ethylene glycol | 2 parts |
| anti-foaming agent | 0.2 parts |
| water | 50.6 parts |

A flowable biocide was obtained by following the same procedures as in Example 1. The biocide had a viscosity of 515 cp.

EXAMPLE 2

| | |
|---|---|
| meta-aldehyde(aldehyde tetramer) | 32 parts |
| polyoxyethylene (5 mol) nonylphenol ether phosphate potassium salt | 5 parts |
| xanthan gum | 0.2 parts |
| ethylene glycol | 2 parts |
| anti-foaming agent | 0.5 parts |
| water | 60.3 parts |

A flowable biocide was obtained by following the same procedures as in Example 1. The resulting flowable biocide was a suspension having a viscosity of 345 cp and a continuous homogeneous phase but not exhibiting flocculation at all.

COMPARATIVE EXAMPLE 2-1

| | |
|---|---|
| meta-aldehyde(aldehyde tetramer) | 32 parts |
| polyoxyethylene (5 mol) nonylphenol ether | 5 parts |
| xanthan gum | 0.2 parts |
| ethylene glycol | 2 parts |
| anti-foaming agent | 0.5 parts |
| water | 60.3 parts |

A flowable biocide was obtained by following the same procedures as in Example 1. The biocide had a viscosity of 750 cp.

COMPARATIVE EXAMPLE 2-2

| | |
|---|---|
| meta-aldehyde(aldehyde tetramer) | 32 parts |
| polyoxyethylene (5 mol) nonylphenol ether phosphate | 5 parts |
| xanthan gum | 0.2 parts |
| ethylene glycol | 2 parts |
| anti-foaming agent | 0.5 parts |
| water | 60.3 parts |

A flowable biocide was obtained by following the same procedures as in Example 1. The pesticide had a viscosity of 620 cp.

EXAMPLE 3

| | |
|---|---|
| Guardside (2-chloro-1-(2,4,5-trichlorophenyl)-vinyl dimethyl phosphate) | 52 parts |
| polyoxyethylene (12 mol) tribenzylphenol ether phosphate diethanolamine salt | 6 parts |
| sodium polyacrylate | 0.5 parts |
| ethylene glycol | 2 parts |
| anti-foaming agent | 0.2 parts |
| water | 39.3 parts |

A flowable biocide was obtained by following the same procedures as in Example 1. The resulting flowable biocide was a suspension having a viscosity of 520 cp and a continuous homogeneous phase but not exhibiting flocculation at all.

COMPARATIVE EXAMPLE 3

| | |
|---|---|
| Guardside (same as in Example 3) | 52 parts |
| polyoxyethylene (12 mol) tribenzylphenol ether | 6 parts |
| sodium polyacrylate | 0.5 parts |
| ethylene glycol | 2 parts |
| anti-foaming agent | 0.2 parts |
| water | 39.3 parts |

A flowable biocide was obtained by following the same procedures as in Example 1. The biocide had a viscosity of 1,200 cp.

EXAMPLE 4

| | |
|---|---|
| sulfur | 52 parts |
| polyoxyethylene (30 mol) tribenzylphenol ether phosphate diethanolamine salt | 3 parts |
| sodium alkylbenzenesulfonate | 3 parts |
| guar gum | 0.5 parts |
| ethylene glycol | 3 parts |
| anti-foaming agent | 0.5 parts |
| water | 38 parts |

A flowable biocide was obtained by following the same procedures as in Example 1. The resulting flowable biocide was a suspension having a viscosity of 580 cp and a continuous homogeneous phase but not exhibiting flocculation at all.

COMPARATIVE EXAMPLE 4

| | |
|---|---|
| sulfur | 52 parts |
| polyoxyethylene (30 mol) tribenzylphenol ether | 3 parts |
| sodium alkylbenzenesulfonate | 3 parts |
| guar gum | 0.5 parts |
| ethylene glycol | 3 parts |
| anti-foaming agent | 0.5 parts |
| water | 38 parts |

A flowable biocide was obtained by following the same procedures as in Example 1. The biocide had a viscosity of 880 cp.

EXAMPLE 5

| | |
|---|---|
| Topzine M (dimethyl 4,4'-o-phenylene-3,3'-dithioallophanate) | 21 parts |
| Thiuram (bis(dimethylthiocarbamyl) disulfite) | 16 parts |

| | |
|---|---|
| polyoxyethylene (12 mol) tribenzyl-phenol ether phosphate diethanol-amine salt | 5 parts |
| polyacrylic acid | 0.2 parts |
| ethylene glycol | 3 parts |
| anti-foaming agent | 0.5 parts |
| water | 54.3 parts |

A flowable biocide was obtained by following the same procedures as in Example 1. The resulting flowable biocide was a suspension having a viscosity of 280 cp and a continuous homogeneous phase but not exhibiting flocculation at all.

COMPARATIVE EXAMPLE 5

| | |
|---|---|
| Topzine (same as in Ex. 5) | 21 parts |
| Thiuram (same as in Ex. 5) | 16 parts |
| polyoxyethylene (12 mol) tribenzyl-phenol ether | 5 parts |
| polyacrylic acid | 0.2 parts |
| ethylene glycol | 3 parts |
| anti-foaming agent | 0.5 parts |
| water | 54.3 parts |

A flowable biocide was obtained by following the same procedures as in Example 1. The biocide had a viscosity of 600 cp.

EXAMPLE 6

| | |
|---|---|
| Stam (3',4'-dichloropropionanilide) | 52 parts |
| polyoxyethylene (7.6 mol) phenylphenol ether phosphate diethanolamine salt | 5 parts |
| sodium alkylbenzenesulfonate | 5 parts |
| xanthan gum | 0.1 parts |
| ethylene glycol | 2 parts |
| anti-foaming agent | 0.5 parts |
| water | 35.4 parts |

A flowable biocide was obtained by following the same procedures as in Example 1. The resulting flowable biocide was a suspension having a viscosity of 490 cp and a continuous homogeneous phase but not exhibiting flocculation at all.

COMPARATIVE EXAMPLE 6

| | |
|---|---|
| Stam (same as in Ex. 6) | 52 parts |
| polyoxyethylene (7.6 mol) phenylphenol ether | 5 parts |
| sodium alkylbenzenesulfonate | 5 parts |
| xanthan gum | 0.1 parts |
| ethylene glycol | 2 parts |
| anti-foaming agent | 0.5 parts |
| water | 35.4 parts |

A flowable biocide was obtained by following the same procedures as in Example 1. The biocide had a viscosity of 1,350 l cp.

EXAMPLE 7

| | |
|---|---|
| Sappiran (p-chlorophenyl p-chlorobenzenesulfonate) | 21 parts |
| Omite (2-(p-tert-butylphenoxy)cyclohexyl propinyl sulfite) | 21 parts |
| polyoxyethylene (12 mol) styrenated phenol ether phosphate diethanolamine salt | 5 parts |
| guar gum | 0.5 parts |
| ethylene glycol | 3 parts |
| anti-foaming agent | 0.5 parts |
| water | 49 parts |

A flowable biocide was obtained by following the same procedures as in Example 1. The resulting flowable biocide was a suspension having a viscosity of 380 cp and a continuous homogeneous phase but not exhibiting flocculation at all.

COMPARATIVE EXAMPLE 7

| | |
|---|---|
| Sappiran (same as in Ex. 7) | 21 parts |
| Omite (same as in Ex. 7) | 21 parts |
| polyoxyethylene (12 mol) styrenated phenol ether | 5 parts |
| guar gum | 0.5 parts |
| ethylene glycol | 3 parts |
| anti-foaming agent | 0.5 parts |
| water | 40 parts |

A flowable biocide was obtained by following the same procedures as in Example 1. The biocide had a viscosity of 620 cp.

TESTING EXAMPLE

The flowable biocides prepared in Examples 1 through 7 and Comparative Examples 1 through 7 were placed in cylinders, having a 3 cm inner diameter and a 12 cm height, to the height of 10 cm and were separately stored for four weeks at 25° C. and 45° C. After the passage of these periods, the suspension ratio, the viscosity and the presence of re-dispersibility were examined. Occurrence of flocculation when each biocide was diluted eight times was also evaluated.

The suspension ratio can be obtained from the following equation:

$$\text{suspension ratio (\%)} = \frac{\text{(original height of suspension)} - \text{(height of supernatant after 4 weeks)}}{\text{original height of suspension}} \times 100$$

Evaluation of re-dispersibility

After the pesticides were stored at 25° C. and 45° C. for 4 weeks, the cylinders containing the flowable biocides were turned down and the presence of hard cake at the bottom of each cylinder was observed. If the hard cake was observed, each cylinder was repeatedly turned down until a uniform suspension was formed and the number of times was counted.

A: no occurrence of hard cake at all
B: 1–5 times
C: 6–10 times
D: 10 times or more Evaluation of presence of flocculation when diluted 8 times 100 ml each suspension was added to 700 ml of hard water of 10 HD and was circulated for 20 minutes using a laboratory pump having a flow rate of 10 l/minute. The suspension was then passed through a 250-mesh sieve and the degree of flocculation was evaluated in accordance with the following standard:

A: no flocculation at all

B: flocculation of about 10 to about 30% was observed.
C: flocculation of about 50% or more was observed.
These results are tabulated in Table 1.

TABLE 1

| | 25° C. | | | | 45° C. | | | |
|---|---|---|---|---|---|---|---|---|
| | suspension ratio (%) | viscosity (cp/20° C.) as-produced | viscosity (cp/20° C.) after storage | re-dispersibility | suspension ratio (%) | viscosity (cp/20° C.) as-produced | viscosity (cp/20° C.) after storage | re-dispersibility | diluted 8 times with 10HD water |
| Example 1 | 100 | 320 | 325 | A | 100 | 320 | 325 | A | A |
| Comp. Ex. 1 | 70 | 515 | 500 | C | 50 | 515 | 425 | D | C |
| Example 2 | 95 | 345 | 345 | A | 92 | 345 | 340 | A | A |
| Comp. Ex. 2-1 | 58 | 750 | 600 | D | 42 | 750 | 500 | D | C |
| Comp. Ex. 2-2 | 66 | 620 | 520 | C | 53 | 620 | 495 | C | B |
| Example 3 | 100 | 520 | 515 | A | 100 | 520 | 510 | A | A |
| Comp. Ex. 3 | 62 | 1200 | 1100 | C | 45 | 1200 | 900 | D | C |
| Example 4 | 100 | 580 | 524 | A | 100 | 580 | 575 | A | A |
| Comp. Ex. 4 | 60 | 880 | 800 | C | 40 | 880 | 400 | D | C |
| Example 5 | 100 | 280 | 295 | A | 100 | 280 | 275 | A | A |
| Comp. Ex. 5 | 68 | 600 | 480 | D | 50 | 600 | 385 | D | C |
| Example 6 | 98 | 490 | 475 | A | 97 | 490 | 475 | A | A |
| Comp. Ex. 6 | 62 | 1350 | 1248 | D | 45 | 1350 | 650 | D | C |
| Example 7 | 100 | 380 | 375 | A | 100 | 380 | 375 | A | A |
| Comp. Ex. 7 | 50 | 620 | 518 | D | 40 | 620 | 280 | D | C |

The embodiments of the invention in which an exclusive property or privilege is claimed are defined as follows:

1. An aqueous biocide suspension consisting essentially of (A) from 10 to 60 wt. % of at least one water-insoluble biocide, (B) from 0.2 to 20 wt. % of a phosphate ester salt of a nonionic surfactant having the formula

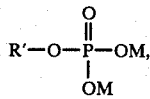

wherein R' is a residue obtained by removing the terminal hydroxy group from a nonionic surfactant having the formula

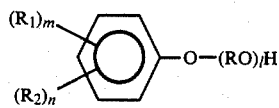

wherein $R_1$ is

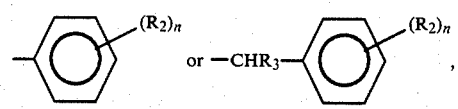

$R_2$ is a $C_1$–$C_4$ alkyl group, $R_3$ is H or $CH_3$, R is a $C_2$–$C_4$ alkylene group, m is an integer of 1 to 3, n is an integer of 0 to 2, l is an integer of 1 to 40, and M is a counter-ion selected from the group consisting of alkali metal, alkaline earth metal, ammonium and alkanolamine, and (C) from 20 to 80 wt. % of water.

2. An aqueous biocide suspension as claimed in claim 1, wherein said suspension additionally contains (D) from 0.01 to 5 wt. % of water-soluble tackifier, and (E) from 0 to 2 wt. % of anti-foaming agent.

3. An aqueous biocide suspension as claimed in claim 2, wherein said suspension contains 1 to 10 wt. % of (B) and 0.05 to 1 wt. % of (D).

4. An aqueous biocide suspension as claimed in claim 1, wherein said water-insoluble biocide is selected from the group consisting of herbicides, fungicides, insecticides, acaricides, and mixtures thereof, and is solid or paste-like at room temperature.

5. An aqueous biocide suspension as claimed in claim 1, wherein M is diethanolamine.

6. An aqueous biocide suspension as claimed in claim 1, wherein said nonionic surfactant is a polyoxyethylene tribenzylphenol ether phosphate diethanolamine salt or a polyoxyethylene phenylphenol ether phosphate diethanolamine salt.

7. A dilute aqueous biocide suspension obtained by diluting the suspension of claim 1 by at least 8 times with water.

8. An aqueous biocide suspension as claimed in claim 1, wherein said biocide is a herbicide.

9. An aqueous biocide suspension as claimed in claim 8, wherein said herbicide is 2-chloro-4-ethylamino-6-isopropylamino-1,3,5-triazine.

10. An aqueous biocide suspension as claimed in claim 2, wherein said water soluble tackifier is selected from the group consisting of xanthan gum, vegetable pectin, gum arabic, guar gum, methylated cellulose, methylated starch derivatives, carboxyalkylated cellulose, carboxyalkylated starch, hydroxyalkylated cellulose, hydroxyalkylated starch, polyacrylates, polymaleates, polyvinylpyrrolidone and mixtures thereof.

11. An aqueous biocide suspension as claimed in claim 1, wherein said suspension further contains one or more anionic or nonionic surfactants selected from the group consisting of alkyl sulfate salts, alkyl ether sulfate salts, alkyl phenyl ether sulfate salts, alkyl naphthalenesulfonate salts, polyoxyethylene alkyl ethers, polyoxyethylene alkyl phenyl ethers, and mixtures thereof.

12. An aqueous biocide suspension as claimed in claim 3, wherein M is diethanolamine, and said nonionic surfactant has the formula:

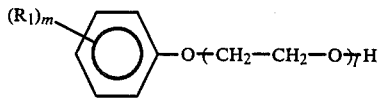

wherein $R_1$ is

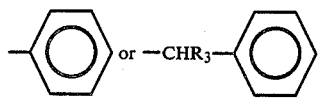

13. An aqueous biocide suspension as claimed in claim 12, wherein said water-insoluble biocide (A) is selected from the group consisting of herbicides, fungicides, insecticides, acaricides and mixtures thereof, said phosphate ester salt of a nonionic surfactant (B) is selected from the group consisting of polyoxyethylene tribenzylphenol ether phosphate diethanolamine salt and polyoxyethylene phenylphenol ether phosphate diethanolamine salt, and said tackifier (D) is selected from the group consisting of xanthan gum, sodium polyacrylate, guar gum, and polyacrylic acid.

14. An aqueous biocide suspension as claimed in claim 13, consisting essentially of 37 to 52 wt.% of (A), 3 to 6 wt.% of (B), 35.4 to 54.3 wt.% of (C), 0.1 to 0.5 wt.% of (D), 0.2 to 0.5 wt.% of (E), and 2 to 3 wt.% of ethylene glycol (F).

15. An aqueous biocide suspension as claimed in claim 14, wherein said phosphate ester salt of a nonionic surfactant (B) is selected from the group consisting of polyoxyethylene (12 mol) tribenzylphenol ether phosphate diethanolamine salt, polyoxyethylene (30 mol) tribenzylphenol ether phosphate diethanolamine salt, and polyoxyethylene (7.6 mol) phenylphenol ether phosphate diethanolamine salt.

16. An aqueous biocide suspension as claimed in claim 15, wherein said biocide (A) is selected from the group consisting of 2-chloro-1-(2,4,5-trichlorophenyl)-vinyl dimethyl phosphate, sulfur, dimethyl-4,4'-o-phenylene-3,3'-dithioallophanate, bis(methylthiocarbamyl)-disulfite, and 3',4'-dichloropropionanilide.

17. A dilute aqueous biocide suspension obtained by diluting the suspension of claim 14 by at least 8 times with water.

18. An aqueous biocide suspension as claimed in claim 14, wherein said biocide composition further contains 3 to 5 wt.% of sodium alkylbenzenesulfonate.

19. An aqueous biocide composition according to claim 3, wherein said anti-foaming agent is polypropylene glycol or silicone oil.

* * * * *